United States Patent [19]
Lyapin et al.

[11] Patent Number: 5,824,207
[45] Date of Patent: Oct. 20, 1998

[54] METHOD AND APPARATUS FOR OXIDIZING AN ORGANIC LIQUID

[75] Inventors: Andrei G. Lyapin, Moscow, Russian Federation; Zakhar R. Khait, Brooklyn, N.Y.

[73] Assignee: Novetek Octane Enhancement, Ltd., New York, N.Y.

[21] Appl. No.: 643,074

[22] Filed: Apr. 30, 1996

[51] Int. Cl.⁶ .................................................. C07C 24/10
[52] U.S. Cl. ........................................... 208/3; 208/4
[58] Field of Search ........................................ 208/3

[56] References Cited

U.S. PATENT DOCUMENTS

| | | | |
|---|---|---|---|
| 521,265 | 1/1894 | Andreoli | 422/186 |
| 4,404,110 | 9/1983 | Beazley et al. | 252/8.55 |
| 4,410,495 | 10/1983 | Bassler et al. | 422/186.18 |
| 4,461,744 | 7/1984 | Erni et al. | 422/186 |
| 4,774,062 | 9/1988 | Heinenmann | 422/186.18 |
| 4,908,189 | 3/1990 | Staubach | 422/186.18 |
| 4,954,321 | 9/1990 | Jensen | 422/186 |
| 4,981,656 | 1/1991 | Leitzke | 422/186.18 |
| 5,554,344 | 9/1996 | Duarte | 422/186 |

FOREIGN PATENT DOCUMENTS

| | | |
|---|---|---|
| 236021 | 9/1987 | European Pat. Off. |
| 57-59988 | 4/1982 | Japan . |
| 59-221386 | 12/1984 | Japan . |
| 62-290793 | 12/1987 | Japan . |
| 1754762 | 8/1992 | Russian Federation . |
| 2036130 | 5/1995 | Russian Federation . |

OTHER PUBLICATIONS

Kam'yanov et al. Sistem, Soviet Acad. of Sciences, pp. 146–165 (1989) (Abstract).
Kam'yanov et al. "Ozonization of Heavy Oils and Resultant Products" Neftekhimimiya, 31, pp. 255–263 (1991) (Abstract).
Sonoda et al., "Desulfurizing Effect of ozone on light petroleum distillate." Kogyo Kasuku Zasshi, $1^2$, p. 1099–1101 (1969) (Abstract).
Kam'yanov et al. "Some Possibilities for the Practical Use of the Process and Products of Ozonolysis of Petroleum Feedstocks" Probl. Khim, Nefti, pp. 348–355 (1992) (Abstract).
English language Abstract of JP 62290793 Dec. 1987.
English language Abstract of JP 59–221386 Dec. 1984.
English language Abstract of JP 5759988 Apr. 1982.
English language Abstract of SU 1754762 May 1992.

*Primary Examiner*—Helane Myers
*Attorney, Agent, or Firm*—Baker & Botts, L.L.P.

[57] ABSTRACT

The present invention relates generally to a method and apparatus for oxidizing an organic liquid, and, more particularly, to a method and apparatus for improving the combustion characteristics of petroleum-based hydrocarbon liquids. The present invention further relates to a method and apparatus for producing an oxidizing gas which comprises substantial amounts of $O_3^{-2}$.

18 Claims, 4 Drawing Sheets

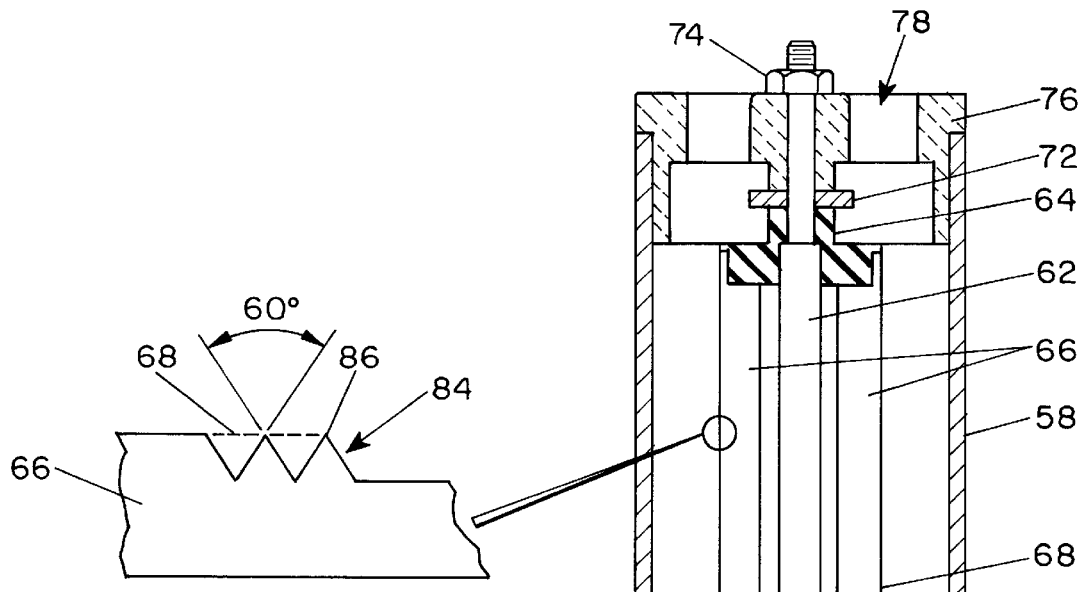
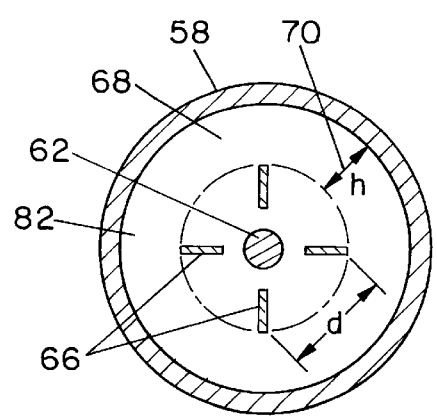
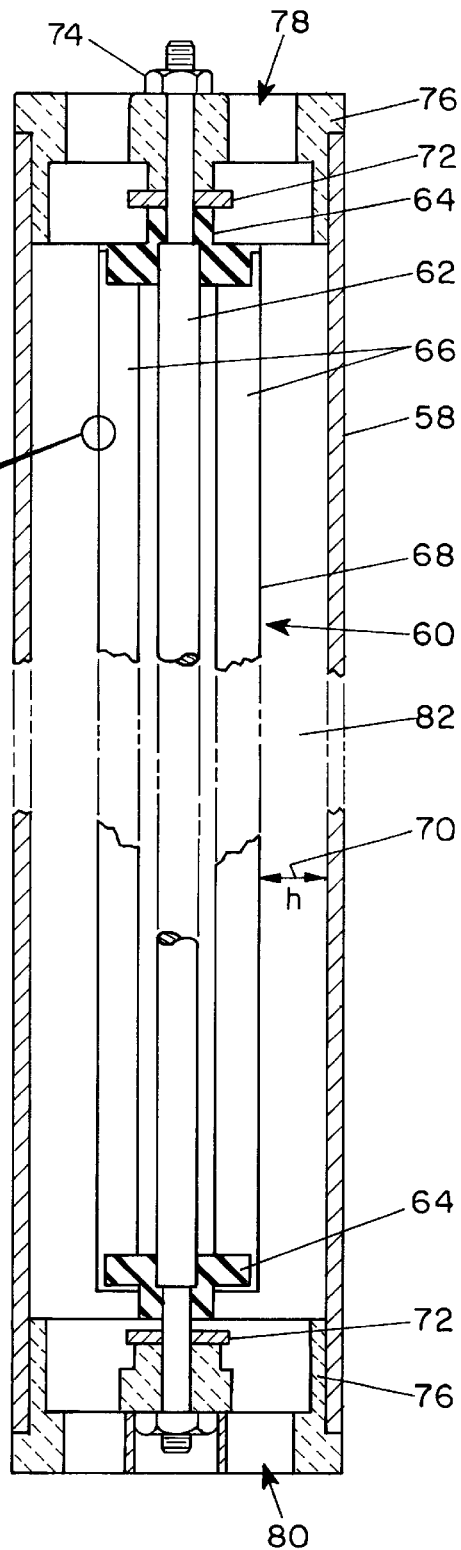
FIG. 2(b)
FIG. 2(c)
FIG. 2(a)

METHOD AND APPARATUS FOR OXIDIZING AN ORGANIC LIQUID

BACKGROUND OF THE INVENTION

The present invention relates generally to a method and apparatus for oxidizing an organic liquid, and, more particularly, to a method and apparatus for improving the combustion characteristics of petroleum-based hydrocarbon liquids. The present invention further relates to a method and apparatus for producing an oxidizing gas which comprises substantial amounts of $O_3^{-2}$.

Petroleum-based hydrocarbon liquids are conventionally refined by subjecting them to a series of heating steps, elevated pressure and a large excess of hydrogen gas. These liquids typically comprise a mixture of various hydrocarbon molecules having a large distribution of molecular weights together with sulfur and nitrogen-containing compounds. Most of the hydrocarbon molecules present in crude oil have molecular weights which are too high to burn efficiently in an internal combustion engine. Therefore, in conventional refining methods, the individual hydrocarbon molecules are successively broken up into lower molecular weight molecules. This process, which is commonly known as cracking, lowers the average molecular weight of the hydrocarbon molecules in the oil, creating more low molecular weight molecules, which typically burn more efficiently in an internal combustion engine.

In conventional refining methods, fractions of crude oil generated during each successive heating step are isolated on the basis of their density and volatility. Specifically, high density fractions will become localized at the bottom of a reactor and low density fractions will become localized near the top of a reactor. High volatility fractions may be separated by extracting and condensing vapor formed within a reactor. It is often necessary to repeat the refining process using the individual fractions to produce acceptable hydrocarbon fuels. The refining process ultimately isolates relatively narrow molecular weight distributions of hydrocarbon molecules which correspond to commercially useful hydrocarbon fuels such as gasoil, home heating oil, diesel fuel, various grades of gasoline and kerosenes.

Conventional refining methods suffer from numerous drawbacks. Specifically, conventional refining methods are expensive because they require supplying large amounts of heat and elevated pressure to provide the energy necessary to cause high molecular weight hydrocarbon molecules to break up into lower molecular weight molecules. Also, conventional refining methods are inefficient because they are incapable of yielding more than about 25% of light fuels, such as gasoline. Moreover, the fuel produced by conventional refining methods contains large amounts of sulfur and nitrogen compounds. When such fuels are burned in internal combustion engines, they produce undesirable pollutants which are harmful to the environment.

Devices for producing ozone ($O_3$) gas are known in the art. Conventional ozone generating devices comprise two closely spaced electrodes which are separated by a narrow gas channel and an insulating material. These devices are operated by subjecting the two electrodes to a high-voltage alternating current while passing dry oxygen through the gas channel. These devices do not work efficiently if a moist oxygen-containing gas, such as atmospheric air, is used in place of the dry oxygen.

The process of ozonolysis is well known in organic chemistry. This process is conventionally performed by intensive exposure of an organic compound to ozone. This process promotes the reactions of hydrogenation and desulfonization.

It is also known to expose hydrocarbon fuels to $O_3$ for the purpose of reducing the amount of environmentally harmful nitrogen and sulfur compounds in hydrocarbon fuels. However, exposing a hydrocarbon molecule to $O_3$ may not be used as a substitute for the above-described cracking process because $O_3$ is not sufficiently oxidizing to break ordinary single carbon-carbon bonds within high molecular weight hydrocarbon molecules.

In view of the foregoing, it would be advantageous to employ an inexpensive, efficient method of refining hydrocarbon liquids which avoids the above described disadvantages of conventional petroleum refining methods. It would also be advantageous to employ an efficient method for producing an oxidizing gas which comprises $O_3^{-2}$, which is more oxidizing than $O_3$. This oxidizing gas may further comprise $O_3^-$, $O_2^-$, $O^-$, $O_3$, $O_2$ and other gases.

Accordingly, it is one object of this invention to provide an efficient method and apparatus for cracking hydrocarbon liquids which does not require heating the hydrocarbon liquid, subjecting the hydrocarbon liquid to elevated pressure, or supplying a large excess of hydrogen gas. It is another feature of the invention that it produces hydrocarbon fuels which are almost totally free of undesirable sulfur and nitrogen compounds without requiring expensive further processing steps specifically directed to removing these compounds. It is yet another feature of the invention that it produces fuels which are free of peroxides, which are undesirable, unstable and potentially explosive compounds. It is an additional feature of the invention that it may be used to increase the percentage yield of light gasolines from treated petroleum-based hydrocarbon liquids, and that it increases the content of alcohols, esters, ethers, ketones and other oxygenated hydrocarbons which enhance the combustion characteristics of the hydrocarbon fuels.

It is another object of the invention to provide an efficient method and apparatus for generating an oxidizing gas which comprises substantial quantities of $O_3^{-2}$. It is a further feature of the invention that it does not require using dried air or oxygen as a starting gas. It is another feature of the invention that the apparatus for generating an oxidizing gas operates efficiently at a voltage of approximately 5 kV per centimeter of the discharge gap, wherein the discharge gap is preferably from 10 to 14 mm.

SUMMARY OF THE INVENTION

The process for oxidizing an organic liquid according to the present invention comprises producing an amount of oxidizing gas which comprises an effective amount of $O_3^{-2}$, and reacting the organic liquid with this gas. The oxidizing gas may further comprise additional species such as $O_3^-$, $O_2^-$, $O^-$, $O_3$, $O_2$ and other gases. In a preferred embodiment of the invention, the oxidizing gas is reacted with the organic liquid by bubbling the gas through the organic liquid under subcritical fluidization conditions.

In a preferred embodiment of the process according to the invention, the organic liquid is a petroleum-based hydrocarbon liquid. Without limiting the invention to any particular theory, it is believed that the oxidizing gas participates in a complex series of chemical reactions with the hydrocarbon liquid, including reactions which are analogous to the cracking process of conventional petroleum refining. However, in contrast with conventional processes for improving the combustion characteristics of a petroleum-based hydrocarbon liquid, the process of the invention does not require heating the liquid, subjecting the liquid to elevated pressure or exposing the liquid to a large excess of hydrogen gas. In a more preferred embodiment of the invention, a petroleum-based hydrocarbon liquid is reacted with a first amount of oxidizing gas, a treated fraction of the petroleum-based hydrocarbon liquid is isolated, and then the treated fraction is further reacted with a second amount of oxidizing gas. In an alternative embodiment of the invention, water is added to the petroleum-based hydrocarbon liquid.

The apparatus for oxidizing an organic liquid according to the present invention comprises an oxidizing gas generating device, a primary reactor vessel, a bubbler and a gas conduit. The oxidizing gas generating device has an oxygen-containing gas entrance aperture and an oxidizing gas exhaust aperture. The gas conduit is attached to the oxidizing gas exhaust aperture and leads to the bubbler, which is inside the primary reactor vessel. The bubbler is located below the maximum filling point of the primary reactor in a position where bubbles produced from the bubbler will achieve maximum contact with the organic liquid. However, it may be advantageous to locate the bubbler above the bottom of the primary reactor to avoid clogging the bubbler with precipitates.

In a preferred embodiment of the apparatus for oxidizing an organic liquid according to the present invention, the gas conduit is interrupted by a compressor which draws gas through the oxidizing gas generating device and forces gas out from the bubbler into the primary reactor. In an alternative embodiment, the compressor may be attached to the oxygen-containing gas entrance aperture of the oxidizing gas generating device to force an oxygen containing gas into the oxygen-containing gas entrance aperture of the oxidizing gas generating device.

The oxidizing gas generating device according to the present invention comprises a gas passage extending between an oxygen-containing gas entrance aperture and an oxidizing gas exhaust aperture. The device further comprises an anode which defines an outer boundary of a discharge gap. The device also comprises a high-voltage cathode which, at its surface closest to the anode, defines an inner boundary of the discharge gap. The gas passage encompasses the discharge gap. Also, the anode and the high-voltage cathode are geometrically arranged to produce a sharply nonuniform electric field therebetween.

In a preferred embodiment of the oxidizing gas generating device, the high-voltage cathode comprises a base axle which extends axially within a tubular anode, and at least one blade plate which is fastened to the base axle. The blade plate extends radially from the base axle toward the tubular anode. The blade plate has a blade plate edge at the outer extreme of the blade plate closest to the tubular anode. The distance between the blade plate edge and the anode is the discharge gap. In a more preferred embodiment to the invention, the blade plate edge has teeth.

The process for producing an oxidizing gas according to the present invention comprises causing an oxygen-containing gas to be fed into an oxygen-containing gas input aperture of the above described oxidizing gas generating device. This process also requires energizing the high-voltage cathode to a sufficiently high potential to cause a repeating torch discharge to emanate from the high voltage cathode. However, the high-voltage cathode must not be energized to a sufficient extent to cause electrical arcing across the discharge gap.

These and other features, aspects and advantages of the present invention will become better understood with reference to the following detailed description, appended claims and accompanying drawings.

BRIEF DESCRIPTION OF THE DRAWINGS

FIG. 2a depicts a sectional side view of a preferred oxidizing gas generating device according to the invention.

FIG. 2b depicts a magnified sectional view of a blade plate edge of the preferred oxidizing gas generating device shown in FIG. 2a.

FIG. 2c depicts a top sectional view of the preferred oxidizing gas generating device shown in FIG. 2a.

DETAILED DESCRIPTION OF THE INVENTION

Figure 1:
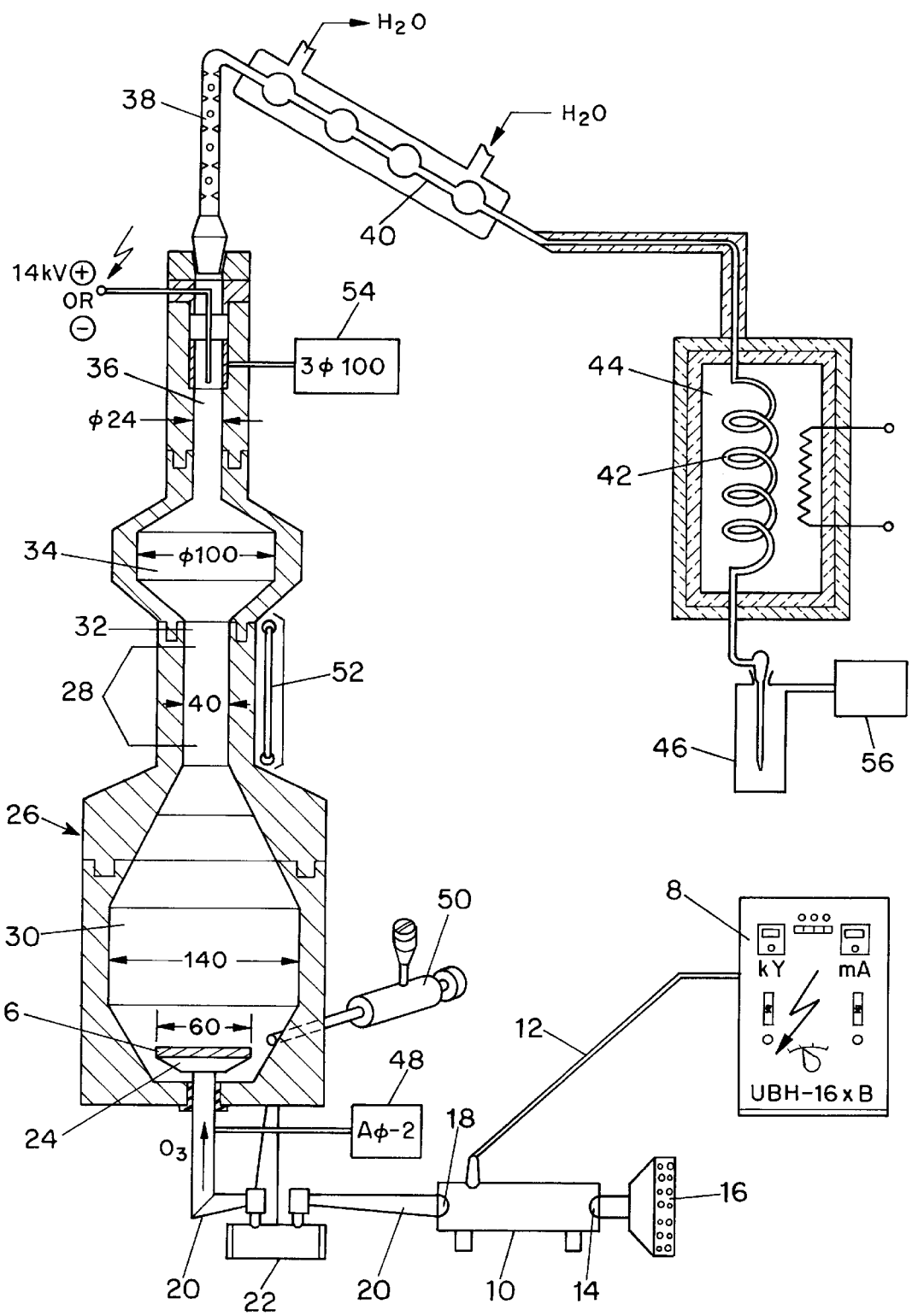
FIG. 1 depicts a diagrammatic view of a preferred apparatus for oxidizing an organic liquid according to the present invention.

The process for oxidizing an organic liquid according to the present invention comprises producing an amount of an oxidizing gas which comprises an effective amount of the ozone anion $O_3^{-2}$, and reacting this oxidizing gas with the organic liquid. The oxidizing gas is preferably generated using the process for producing an oxidizing gas described herein. In a preferred embodiment of the invention, the oxidizing gas comprises at least 1 gram $O_3^{-2}$ per cubic meter of the organic liquid. In a more preferred embodiment of the invention, the oxidizing gas comprises at least 3 grams $O_3^{-2}$ per cubic meter of the organic liquid. In an even more preferred embodiment of the invention, the total amount of oxidizing gas passed through the organic liquid is from 10 to 150 grams per cubic meter of the organic liquid. In a most preferred embodiment of the present invention, the oxidizing gas comprises about 40% $O_3^{-2}$.

In a preferred embodiment of the invention, a petroleum-based hydrocarbon liquid is treated with the oxidizing gas. Without limiting the invention to any particular theory, it is believed that the oxidizing gas oxidizes the petroleum-based hydrocarbon liquid, thereby improving its combustion characteristics. Specifically, it is believed that the ozone anions are sufficiently oxidizing to cause reactions which break single carbon-carbon bonds within the hydrocarbon molecules. It is further believed that the oxidizing gas causes conversion of double carbon-carbon bonds in unsaturated hydrocarbons into single carbon-carbon bonds in saturated hydrocarbons. It is also believed that the oxidizing gas causes conversion of double bonds in aromatic compounds into single bonds in alicyclic compounds. The process of the invention is believed to lower the average molecular weight of the hydrocarbon molecules, which creates a hydrocarbon liquid with better combustion characteristics for internal combustion engines.

The process of the invention is also thought to improve the suitability of hydrocarbon liquids for use as fuel in internal combustion engines because the process causes conversion of sulfur into sulfates and sulfides, which then precipitate. It is advantageous to be able to oxidize and remove these sulfur compounds because untreated sulfur causes pollution in the exhaust of internal combustion engines. In contrast, oxidized sulfur compounds may act as beneficial lubricants in internal combustion engines and do not cause pollution. It is further believed that the oxidizing gas causes various other reactions with the petroleum-based hydrocarbon liquid which include oxidation of undesirable nitrogen-containing compounds, free-radical reactions such as hydrogen abstraction, hydrogenation and formation of alcohols, ethers, ketones, esters and other oxygen-containing organic compounds. It is also believed that additional $O_3^{-2}$ is generated when the oxidizing gas is bubbled through the petroleum-based hydrocarbon. This additional $O_3^{-2}$ is thought to be formed by the reaction of hydrogen peroxide with ozone.

In a preferred embodiment of the present invention, the oxidizing gas is bubbled through a petroleum-based hydrocarbon liquid under conditions of subcritical fluidization. Specifically, the oxidizing gas is preferably forced out of a porous bubbler output material (porosity $\geq 85\%$) on the surface of a bubbler located near the bottom of a vertical reactor which contains an amount of the petroleum-based hydrocarbon liquid. In a more preferred embodiment of the invention, the bubbles have a starting size of from 20 to 50 microns.

Subcritical fluidization is a process analogous to forming an ebbulated fluidized bed with the exception that, in a conventional fluidized bed reactor, a gas is passed through a powder to achieve a fluidized bed. However, in the present case, a gas is passed through a liquid to achieve a "fluidized" gas/fluid system. In the present case, as in a conventional fluidized bed, the volume of the medium being fluidized expands. In the present embodiment, the volume of the organic fluid typically expands to about 2.3 to 3.5 times its initial volume. A foam is also created on the surface of the organic liquid. The condition of subcritical fluidization involves turbulent flow of the bubbles through the organic liquid. The bubbles of oxidizing gas have their smallest diameter at the bottom of the reactor, and increase in size as they travel toward the surface of the organic liquid.

In another embodiment of the present invention, different fractions of the petroleum-based hydrocarbon liquid are separated and optionally further treated using the present method. Typically, the products having high vapor pressure formed during the process are isolated by affixing a condensing system to the top of the reactor which isolates vapors generated during the treatment process. In one embodiment of the invention, the condensing system comprises a dephlegmater linked to a water-cooled condenser, which is in turn attached to a coil condenser housed within a refrigeration chamber. In a more preferred embodiment of the invention, petroleum-based hydrocarbon liquid fractions having differing densities are isolated by withdrawing fractions of the treated liquid from different heights within the reactor. An isolated fraction may then be treated a second time using an additional amount of oxidizing gas.

In an alternative embodiment of the invention, water is added to the petroleum-based hydrocarbon liquid. It is believed that the water may serve as a hydrogen source, replacing the large amounts of hydrogen gas which must be used in conventional refining processes. It is further believed that the water may also react with the oxidizing gas to produce $H^+$ and $OH^-$ ions, which are known to be instrumental in promoting the free radical reaction mechanisms.

A preferred embodiment of the apparatus for oxidizing an organic liquid according to the invention comprises a primary reactor vessel which contains a bubbler. All parts of the apparatus which come in contact with the oxidizing gas are preferably made of corrosion resistant materials such as stainless steel. The bubbler has a porous bubbler output material which separates the interior of the bubbler from the interior of the primary reactor vessel. A gas conduit leads from the bubbler to the ozone-anion oxidizing gas exhaust aperture of an ozone-anion oxidizing gas generating device.

In a preferred embodiment of the apparatus for oxidizing an organic liquid according to the invention, the apparatus for oxidizing an organic liquid further comprises a compressor which is affixed to the gas conduit between the bubbler and the oxidizing gas exhaust aperture of an ozone-anion oxidizing gas generating device. In an alternative less preferred embodiment of the invention, a compressor is affixed to the oxygen-containing gas input aperture of the oxidizing gas generating device.

In a more preferred embodiment of the apparatus for oxidizing an organic liquid, the bubbler is located above the bottom of the primary reactor so that precipitates generated during the treatment process do not clog the bubbler. The bubbler must be located below the maximum fill point of the primary reactor, and is preferably located near the bottom of the primary reactor to enable maximum contact between the bubbles and the liquid. The bubbler preferably has a porosity of at least 85%, and a permeability of at least $5*10^{-8}\,m^2$. The bubbler is preferably made of a corrosion-resistant material such as a sintered disk of TiN particles.

In another preferred embodiment, the apparatus for oxidizing an organic liquid has a vapor condensing system for isolating any vapors produced during the reaction. This vapor condensing system preferably comprises a condenser which is cooled below room temperature.

In yet another preferred embodiment, the apparatus for oxidizing an organic liquid has one or more input filters for shunting treated fractions of the organic liquid to secondary reactor systems. These input filters are preferably located at different heights within a vertical reactor to enable isolation of different treated fractions of the organic liquid on the basis of density. These input filters are preferably designed to avoid forming a vortex within the liquid which could possibly interfere with subcritical fluidization. (See FIG. 4).

FIG. 1 depicts a bench-top embodiment of an apparatus for oxidizing a petroleum-based hydrocarbon liquid according to the present invention. This embodiment performs the process of the invention, but has not yet been optimized for industrial application. One skilled in the art would be able to easily adapt this embodiment for industrial application. Applicants further note that prophetic example 2 provides some guidance as to how industrial scale-up might be accomplished.

In FIG. 1, an oxidizing gas generating device 10 is connected by high voltage cable 12 to a high voltage power source 8. The oxidizing gas generating device 10 has an oxygen-containing gas entrance aperture 14. The oxygen-containing gas entrance aperture 14 is connected to a dust filter 16. The oxidizing gas generating device 10 also has an oxidizing gas exhaust aperture 18, which in turn is affixed to a gas conduit 20. The gas conduit 20 is interrupted by a compressor 22 and leads to a bubbler 24, which is located in a primary reactor vessel 26. The primary reactor vessel 26 is a vertical reactor approximately 2 meters tall. The upper surface of the bubbler 24 comprises a porous bubbler output material 6, which is a 3 mm thick sintered disk of TiN having a porosity of approximately 85%. The primary reactor vessel 26 comprises a narrowed fluidization zone 28, which is approximately 1 meter tall, above a lower working volume 30. A maximum fill point 32 is located within the narrowed fluidization zone 28. An expander 34 is adjoined to the top of the narrowed fluidization zone 28. A vapor passage 36 is adjoined to the top of the expander 34. A vertical needle dephlegmater 38 is joined to the top of the vapor passage 36.

A water jacket condenser 40 is joined to the vertical needle deflegmater 38. The output of the water jacket condenser 40 passes into a coil condenser 42, which is housed inside a refrigerating chamber 44. The output of the coil condenser 42 then passes out of the refrigeration chamber 44 into a collector 46.

The embodiment shown in FIG. 1 also shows an ozonometer 48 connected to the gas conduit 20. The embodiment further shows a water injection device 50 which is attached to the lower working volume 30 of the primary reactor vessel 26. The embodiment of the invention shown in FIG. 1 also has an ultraviolet light source 52 which irradiates the narrowed fluidization zone 28. An ion counter 54 is also shown vented to the vapor passage 36. FIG. 1 also depicts a gas analyzer 56 for analyzing the output of the collector 46.

An embodiment of the oxidizing gas generating device of the present invention comprises a gas passage extending between an oxygen-containing gas entrance aperture and an oxidizing gas exhaust aperture. The oxidizing gas generating device further comprises an anode which defines an outer boundary of a discharge gap, and a high-voltage cathode which, at its surface closest to the anode, defines an inner boundary of the discharge gap. The gas passage encompasses the discharge gap. Also, the anode and the high-voltage cathode are preferably arranged in a geometry which produces a sharply nonuniform electric field therebetween. A preferred embodiment of the oxidizing gas generating device according to the present invention is shown in FIG. 2(*a*)–(*c*).

FIG. 2(*a*) depicts an embodiment of the oxidizing gas generating device. The oxidizing gas generating device has a high voltage cathode 60 which is centered inside a tubular anode 58. The high voltage cathode comprises a cathode base axle 62 which is attached via a blade plate holder sleeve 64 to the blade plates 66. The blade plates 66 have blade plate edges 68. The blade plate edges 68 are separated from the tubular anode 58 by the discharge gap 70. The high voltage cathode 60 is centered within the tubular anode 58 by means of a stretching nut 72 and a fastening nut 74. The tubular anode 58 is electrically isolated from the high voltage cathode 60. The bearing isolator 76 helps maintain this electrical isolation. The oxidizing gas generating device also has an oxygen-containing gas entrance aperture 78 and an oxidizing gas exhaust aperture 80. A gas passage 82 joins the oxygen-containing gas entrance aperture 78 and an oxidizing gas exhaust aperture 80. The gas passage 82 encompasses the discharge gap 70.

FIG. 2(*b*) depicts a magnified view of a blade plate edge 68. FIG. 2(*b*) shows that the blade plate edge 68 has a plurality of teeth 84. Each tooth 84 has an apex 86 which forms an angle of approximately 60°.

FIG. 2(*c*) depicts a top cut away view of the oxidizing gas generating device. FIG. 2(*c*) shows that the distance "d" between the blade plate edges 68 of adjacent blade plates 66 is approximately equal to the discharge gap 70. It is undesirable for the distance "d" between adjacent blade plate edges to be smaller than the discharge gap 70, because this will lead to interference between torch discharges emanating from adjacent blade plate edges 68. It is preferred for the distance "d" to be approximately equal to the discharge gap 70.

A more preferred embodiment of the oxidizing gas generating device has blade plates 66 with a thickness of between 50 and 350 micrometers. A further preferred embodiment of the oxidizing gas generating device has teeth 84 which have an apex 86 with a radius of curvature of at least 20 microns, wherein each apex 86 of adjacent teeth is approximately ten times the blade plate thickness. In a most preferred embodiment of the oxidizing gas generating device, the discharge gap 70 is between 10 and 14 mm and the active blade plate length is less than 1.5 meters.

The process for producing an oxidizing gas according to the invention comprises causing an oxygen-containing gas to pass into an oxygen containing gas entrance aperture of an oxidizing gas generating device according to the invention, and energizing the high-voltage cathode to a sufficiently high potential to cause a repeating plasma torch discharge to emanate from the high-voltage cathode, wherein the potential is not sufficiently high to cause electrical arcing across the discharge gap. In order to prevent arcing, the maximum power which may be applied to the oxidizing gas generating device is represented by equation I: Equation II represents the maximum concentration of $O_3$, $O_3^-$, $O_3^=$, $O_2-$ and $O^-$ which may be generated from air according to this method. Equation III represents the flow rate of gas in the discharge gap.

$$P\max = \frac{\lambda \cdot f}{2} \cdot J_p V^3 \cdot s = \frac{\lambda \cdot f}{2} \cdot \frac{I_p}{s} \cdot \left(\frac{Q}{s}\right)^3 \cdot s = 0.4 f\lambda \quad \text{EQUATION I}$$

$$C\max = 0.06 \frac{I_p}{Q} \approx 15 \text{ g/m}^3 \quad \text{EQUATION II}$$

$$V = \frac{Q}{S} = \frac{Q}{n \cdot l_a \cdot \pi(d - 2h)} \quad \text{EQUATION III}$$

wherein,

Pmax=maximum power which can be applied without arcing,

Cmax=maximum concentration of oxidizing gas which may be generated from air, a=distance between blade plate edges of adjacent blade plates (m), h=distance between blade plate edges and the anode (m), Q=flow of gas through the device (m³/hour), $l_a$=active length of blade plate electrodes (m), $U_n$=voltage applied across discharge gap (kV), $I_p$=constant component of discharge current (A), d=inside diameter the anode (m), λ=radiation wavelength (cm), f=frequency of electron beam ($S^{-1}$), s=cross section of torch discharge (m²), V=flow rate of gas in the discharge gap (m/hour), and $J_p$=density of the discharge current (coulomb/m²).

In the above formula, $l_a$ is preferably less than 1.5 meters, $I_p$ is preferably between 0.5 and 35 milliamps, s is preferably about 0.1 mm and $J_p$ is preferably about 80 A/m².

In a preferred embodiment of the invention, $U_n$ is between 12 and 16 kV.

In a most preferred embodiment of the process for producing an oxidizing gas according to the invention, a repeating torch discharge is generated which has a core with the properties of a low temperature plasma. The torch discharge emanates from the apex 86 of the teeth 84 of the high-voltage cathode blade plate edge 68. This discharge creates a strong pulse of ultraviolet light in the 170 to 350 nm range. Without limiting the invention to any one particular theory, it is thought that about 20% of the $O_3^{-2}$ is generated through a photochemical reaction involving the ultraviolet light, and the remainder is generated within the low temperature plasma. In a preferred embodiment of the invention where the discharge gap is 13 mm and 12 kV is applied to the high-voltage cathode, the repeating torch discharge has a length of about 50 nanoseconds and an on-off cycle frequency of about 160 kHz.

The torch discharge generated in the oxidizing gas generator differs from typical ozone generators which contain an insulating material between the anode and cathode. These conventional devices generate a corona discharge, which does not have regions with properties similar to a low temperature plasma. Moreover, the process of the present invention operates using filtered atmospheric air, whereas conventional devices typically require dried oxygen.

Although the present invention has been described in considerable detail with reference to certain preferred versions thereof, other versions are possible without departing from the spirit and scope of the invention. Therefore the appended claims should not be limited to the description of the preferred embodiments of the invention described herein.

The following examples are directed to embodiments of the invention which are useful in the petroleum industry. It should be noted, however, that the invention may also be employed to advantage in producing chemicals for the perfume industry. Moreover, it should be noted that the invention may also be useful for treating paper pulp. Also, the invention may be useful for other applications which conventionally employ ozone gas.

EXAMPLE 1

Bench Top Process for Enhancing the Oxidation Process of an Organic Liquid

In this example, the apparatus shown in FIGS. 1 and 2 was used to treat standard diesel fuel from the Kopotkinsky Refinery according to the process of the present invention. This example was repeated ten times with slight variations. First, for each experiment approximately 0.5 L of diesel fuel was added by pouring the fuel into to the primary reactor vessel 26. The fuel was then allowed to settle for five minutes.

The compressor 22 was next switched on, which caused a gas flow rate of between 0.3 liters per minute and 0.5 liters per minute to emanate from the porous bubbler output material 6 of the bubbler 24. The size of the bubbles was approximately 50 microns at the depth just above the bubbler. A sufficient time delay was allotted for the bubbling to cause steady state subcritical fluidization conditions to develop inside the primary reactor vessel 26. This time delay was approximately 30 seconds.

The high voltage power source 8 for the oxidizing gas generating device 10 was then adjusted to approximately 12 kV. The current produced at this voltage was approximately 30 milliamps. The oxidizing gas generating device 10 used in this experiment had 6 stainless steel blade plates 66 which each had a thickness of approximately 50 microns. These blade plates 66 had blade plate edges 68 with teeth 86. The teeth 84 were evenly spaced equillateral triangles, and the apex 86 of each tooth had a radius of curvature of at least 20 microns. The apex 86 of each tooth 84 had an angle of 60°. The discharge gap 70 and the distance between the blade plate edges "d" was approximately 13 mm. The inside diameter of the anode 58 was approximately 70 mm, and the blade plate 66 length was about 0.5 meters.

The total amount of oxidizing gas passed through the diesel fuel for this experiment was approximately 12 grams per cubic meter of the diesel fuel. The total amount of $O_3^{-2}$ bubbled through the diesel fuel during this experiment was between 2 and 4 grams. The experiments were run for about 12 minutes. No water was added to the diesel fuel during these experiments.

After 12 minutes, the high-voltage power source 8 for the oxidizing gas generating device 10 was shut off. Then the compressor 22 was shut off, and the treated diesel fuel was allowed to settle for between 5 and 30 minutes. After each trial, the treated diesel fuel was analyzed and the primary reactor vessel was washed with untreated diesel fuel before the next run.

Figure 3:
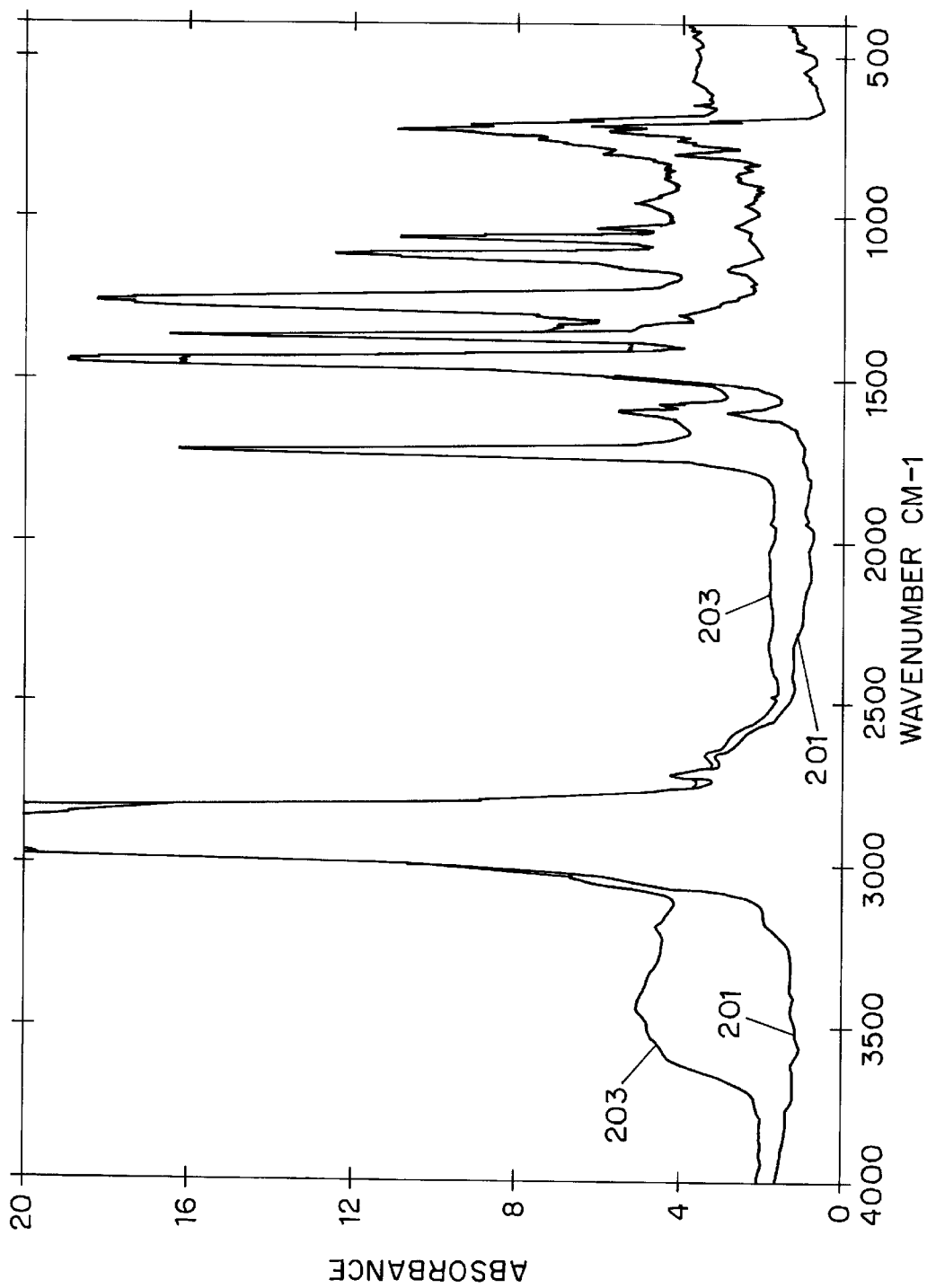
FIG. 3 depicts an infrared spectrometry plot of absorbance versus wavelength ($cm^{-1}$) for untreated diesel fuel and for diesel fuel treated according to the present invention.

FIG. 3 depicts a typical infrared spectrometry plot of absorbance versus frequency ($cm^{-1}$) for untreated diesel fuel 201 which was used as the test fluid for these experiments versus diesel fuel treated according to the present invention 203. The treated diesel fuel shows peaks for alcohols (3400 $cm^{-1}$), ethers (1200 $cm^{-1}$), esters (1280–1670 $cm^{-1}$), ketones (1730 $cm^{-1}$) and ozonides (620 $cm^{-1}$) which are not present in the untreated fuel. Also, the treated diesel fuel shows a peak for combustible sulfates and sulfides (1200 $cm^{-1}$).

The product produced according to the above-described process comprises up to 2–5% alcohols and ethers, up to 25% light gasolines having better than 92 octane, 20–30% light gasolines having less than 76 octane and purified gasoil having substantially no sulfur, undesirable nitrogen compounds or peroxides.

PROPHETIC EXAMPLE 2

Figure 4:
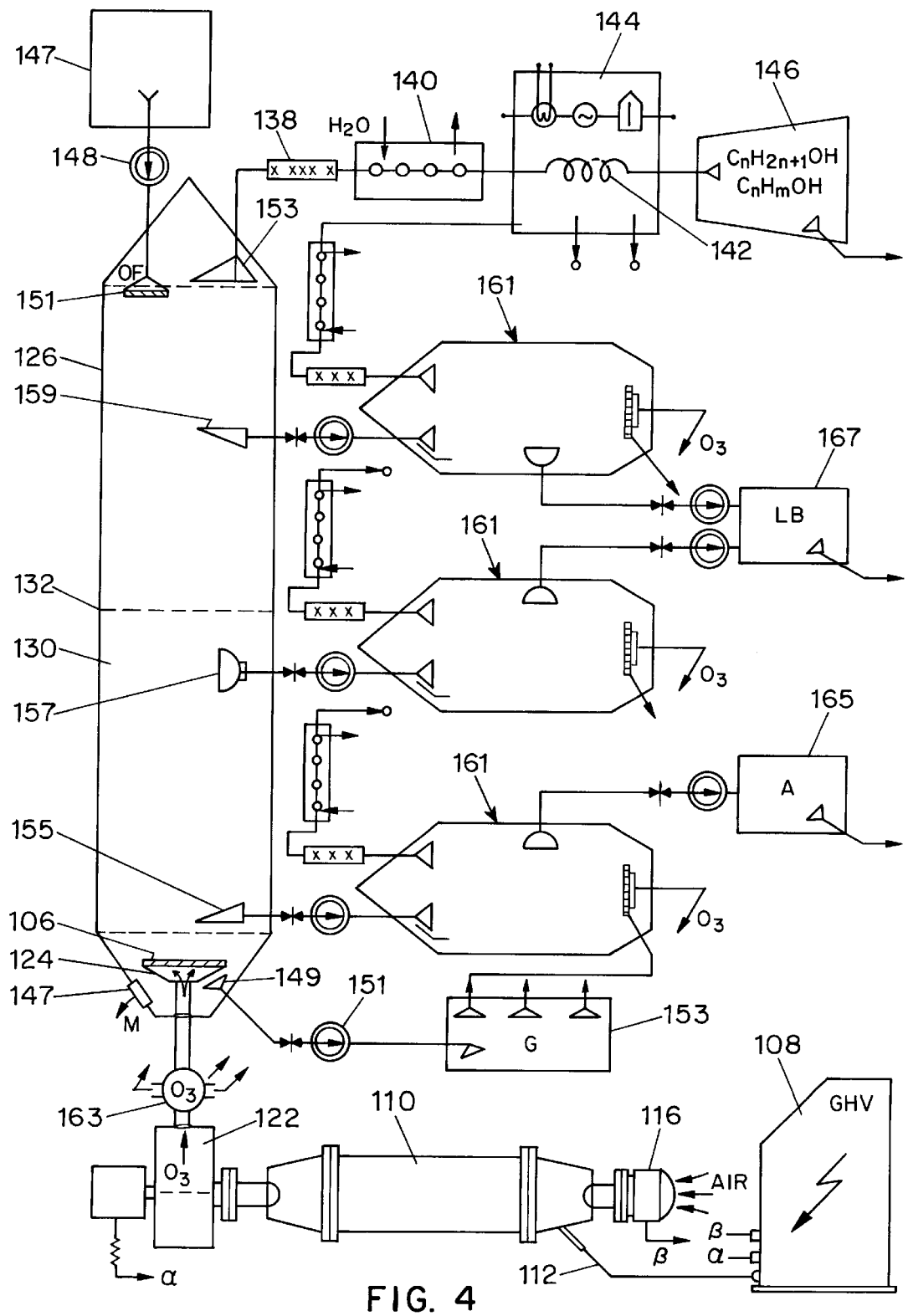
FIG. 4 depicts a diagrammatic view of a prophetic example apparatus according to the invention for oxidizing an organic liquid.

Proposed Industrial Scale-Up of the Process for Oxidizing a Petroleum-Based Hydrocarbon Liquid FIG. 4 depicts a proposed industrial scale-up of the bench top apparatus shown in FIG. 1. The apparatus shown in FIG. 4 is a system having a primary reactor vessel 126 large enough to treat approximately 20 liters of a hydrocarbon liquid. This apparatus is intended to be capable of separating fractions of a hydrocarbon liquid and further treating these fractions. As an example, if a hydrocarbon liquid known as distilled fraction, which has an octane level below 30%, is treated in the primary reactor vessel 126, it is intended that a diesel fuel will be isolated in the heavy fractions retaining tank 153. It is further intended that a lower octane gasoline will be isolated in the lower fractions isolation tank 165 and that a higher octane gasoline will be isolated in the higher fractions isolation tank 167. It is also intended that aliphatic and aromatic alcohols will be collected in the vapor fractions retaining tank 146.

FIG. 4 shows an oxidizing gas generator 110 which is connected by high voltage cables 112 to a high voltage power source 108. The oxidizing gas generator 110 may comprise a boiler system of several linked individual oxidizing gas generators. The oxidizing gas generator 110 is connected to a compressor 122. The compressor 122 is connected to the oxidizing gas distribution system 163. The distribution system 163 feeds gas to the bubbler 124 which comprises a porous bubbler output material 126 on the upper surface. The porous bubbler output material 106 is preferably made of a corrosion resistant material, such as sintered TiN powder, and has a porosity of over 85%. A suitable material is commercially available from PO Powdered Metallurgy in Minsk. The bubbler 124 is contained within the primary reactor vessel 126. The primary reactor vessel 126 also has a sludge removal door 147 which facilitates removal of sediments, such as oxidized sulfur compounds, from the treated petroleum based product. A heavy fractions vortex free intake filter 149 is also located within the primary reactor vessel 126 below the bubbler 124. This vortex free filter 149 is connected by a pump 151 to a heavy fractions retaining tank 153. The primary reactor vessel 126 also contains, in ascending order, a lower fractions vortex free input filter 155, a medium fractions vortex free input filter 157, and a higher fractions vortex free input filter 159. These three vortex free input filters are connected to secondary oxidizing gas treatment systems 161. In FIG. 4, the lower fractions vortex free input filter 157 leads to a secondary oxidizing gas treatment system, which leads to a lower fractions isolation tank 165. The medium fractions vortex free input filter 157 and higher fractions vortex free input filter lead to a higher fractions isolation tank 167.

The starting product reservoir 147 is connected by a pump 148 to an oil filter 151, which empties into the top of the primary reactor vessel 126. The top of the primary reactor vessel 126 also has a vapor collection system which comprises a vapor collecting funnel 153, which feeds into a needle dephlegmater 138, which in turn feeds into a water jacket condenser 140. The output of the water jacket condenser 140 leads into a coil condenser 142, which is located inside a refrigerator 144. The output of the condenser coil 142 leads out of the refrigerator 144 into a vapor fractions retaining tank 146.

It should be noted that the oxidizing gas distribution system 163 also supplies oxidizing gas to the secondary reactor systems 161. It should further be noted that the secondary reactor systems 161 also have vapor collecting systems.

The primary reactor vessel 126 shown in FIG. 4 has a substantially cylindrical shape. However, different bubbler shapes may be used to promote subcritical fluidization. It may also be advantageous to vary the shape within the primary reactor vessel 126 above the bubbler 124 to help promote the formation of turbulence.

We claim:

1. A process for converting an organic liquid comprising a mixture of higher molecular weight hydrocarbons into a mixture comprising lower molecular weight hydrocarbons, said method comprising:

(a) generating an oxidizing gas which comprises $O_3^{-2}$, and (b) reacting the organic liquid with the oxidizing gas, thereby converting the mixture of higher molecular weight hydrocarbons into a mixture comprising lower molecular weight hydrocarbons.

2. The process for converting an organic liquid according to claim 1, wherein the first amount of oxidizing gas is reacted with the organic liquid by bubbling the first amount of oxidizing gas through the organic liquid under conditions sufficient to achieve subcritical fluidization.

3. The process for converting an organic liquid according to claim 2, wherein the first amount of oxidizing gas comprises at least 1 gram of $O_3^{-2}$ per cubic meter of the organic liquid.

4. The process for converting an organic liquid according to claim 3, wherein said first amount of oxidizing gas comprises at least 3 grams of $O_3^{-2}$ per cubic meter of the organic liquid.

5. The process for converting an organic liquid according to claim 4, wherein the step of producing the first amount of oxidizing gas comprises:

(a) feeding an oxygen-containing gas through a gas passage within an oxidizing gas generating device, wherein the oxidizing gas generating device has an anode and a high-voltage cathode and wherein the gas passage includes a discharge gap which separates the high-voltage cathode from the anode, and (b) applying an electrical potential difference between the high-voltage cathode and anode which produces a sharply nonuniform electric field therebetween, such that a repeating torch discharge develops within the discharge gap.

6. The process for converting an organic liquid according to claim 5, wherein the repeating torch discharge emanates from the high-voltage cathode.

7. The process for converting an organic liquid according to claim 6, wherein the cathode comprises a plurality of blade plates each having a blade plate edge with teeth, the teeth each having an apex, wherein the repeating torch discharge emanates from the apex.

8. The process for converting an organic liquid according to claim 4, wherein the organic liquid is a petroleum-based hydrocarbon liquid.

9. The process for converting an organic liquid according to claim 8, wherein the first amount of oxidizing gas is reacted with the petroleum-based hydrocarbon within a vertical reactor.

10. The process for converting an organic liquid according to claim 9, wherein the oxygen-containing gas is filtered air.

11. The process for converting an organic liquid according to claim 9, wherein water is added to the petroleum-based hydrocarbon liquid.

12. The process for converting a petroleum-based hydrocarbon liquid according to claim 9, which further comprises isolating a treated fraction of the petroleum-based hydrocarbon liquid after reacting the petroleum-based hydrocarbon liquid with the first amount of oxidizing gas.

13. The process for converting an organic liquid according to claim 12, wherein the oxidized fraction of the petroleum-based hydrocarbon liquid is isolated by allowing the petroleum-based hydrocarbon liquid to settle after the bubbling step, thereby forming a layer of liquid corresponding to the oxidized fraction of the petroleum-based hydrocarbon liquid within the vertical bubbling reactor, and withdrawing the layer of liquid.

14. The process for converting an organic liquid according to claim 13, wherein after the oxidized fraction of the petroleum-based hydrocarbon is isolated, a second amount of oxidizing gas is bubbled through the isolated fraction of the oxidized petroleum-based hydrocarbon liquid under conditions sufficient to achieve subcritical fluidization, wherein the second amount of oxidizing gas comprises at least 1 gram of $O_3^{-2}$ per cubic meter of the isolated fraction of the petroleum-based hydrocarbon liquid.

15. The process for converting an organic liquid according to claim 9, wherein the petroleum-based hydrocarbon liquid is crude oil and wherein the process further comprises pre-heating the crude oil to a temperature sufficient to lower the viscosity of the crude oil such that subcritical fluidization may be achieved.

16. The process for converting an organic liquid according to claim 9, wherein the petroleum-based hydrocarbon liquid is selected from the group consisting of home heating oil, gasoil, diesel fuel, gasoline and kerosene.

17. The process for converting an organic liquid according to claim 9, wherein the process is conducted at room temperature.

18. The process for converting an organic liquid according to claim 17, wherein the process is conducted at ambient pressure.

* * * * *